(12) United States Patent
Johnson et al.

(10) Patent No.: US 11,083,845 B2
(45) Date of Patent: Aug. 10, 2021

(54) APPARATUS AND METHOD FOR NEUTRALIZING LOCAL ANESTHETIC

(71) Applicant: DEVICE AND APPARATUS LLC, Draper, UT (US)

(72) Inventors: Christopher Shaun Johnson, Draper, UT (US); Trevor K Hanson, Alpine, UT (US); Paul Witherspoon Scott, IV, San Luis Obispo, CA (US)

(73) Assignee: DEVICE AND APPARATUS LLC, Draper, UT (US)

( * ) Notice: Subject to any disclaimer, the term of this patent is extended or adjusted under 35 U.S.C. 154(b) by 306 days.

(21) Appl. No.: 16/225,289

(22) Filed: Dec. 19, 2018

(65) Prior Publication Data

US 2019/0184103 A1  Jun. 20, 2019

Related U.S. Application Data

(60) Provisional application No. 62/608,144, filed on Dec. 20, 2017.

(51) Int. Cl.
*A61M 5/24* (2006.01)
*A61K 9/00* (2006.01)
(Continued)

(52) U.S. Cl.
CPC ............ *A61M 5/2448* (2013.01); *A61J 1/062* (2013.01); *A61J 1/2013* (2015.05); *A61J 1/2089* (2013.01);
(Continued)

(58) Field of Classification Search
CPC .. A61M 5/2448; A61M 5/28; A61M 5/31596; A61M 5/3294; A61M 3/005;
(Continued)

(56) References Cited

U.S. PATENT DOCUMENTS 4,689,042 A * 8/1987 Sarnoff ............... A61M 5/2066
604/89
6,021,824 A * 2/2000 Larsen ................. A61J 1/2089
141/329
(Continued)

OTHER PUBLICATIONS

International Search Report and Written Opinion issued in PCT/US18/66969 dated Mar. 18, 2019.

*Primary Examiner* — Brandy S Lee
*Assistant Examiner* — Hong-Van N Trinh
(74) *Attorney, Agent, or Firm* — Workman Nydegger (57) ABSTRACT

The present disclosure relates to devices and methods for neutralizing an acidic anesthesia solution. An anesthesia neutralization device includes an outer housing and an inner housing. The inner housing holds a buffer carpule and an anesthetic carpule in a side by side arrangement, with the buffer solution maintained under pressure prior to deployment. A curved transfer needle is coupled to the outer housing and includes ends that both point respectively toward the buffer carpule and anesthetic carpule. The device is actuated by moving the inner housing relative to the outer housing to bring the anesthesia carpule and buffer carpule into contact with the transfer needle and to force buffer solution through the transfer needle and into the anesthesia carpule.

21 Claims, 8 Drawing Sheets

(51) Int. Cl.
*A61K 31/167* (2006.01)
*A61J 1/06* (2006.01)
*A61J 1/20* (2006.01)
*A61M 5/28* (2006.01)

(52) U.S. Cl.
CPC .......... *A61K 9/0019* (2013.01); *A61K 31/167* (2013.01); *A61M 5/2425* (2013.01); *A61M 5/28* (2013.01); *A61J 1/2096* (2013.01)

(58) Field of Classification Search
CPC .... A61M 5/2425; A61M 5/2422; A61M 5/24; A61M 2005/2403; A61M 2005/2414; A61M 2005/2407; A61M 2005/2411; A61M 5/284; A61M 2005/2451; A61M 5/19; A61M 5/1782; A61J 1/2096; A61J 1/20; A61J 1/2003; A61J 1/2006; A61J 1/201; A61J 1/2013; A61J 1/2017; A61J 1/06; A61J 1/062; A61J 1/065; A61J 1/2089

See application file for complete search history.

(56) References Cited

U.S. PATENT DOCUMENTS

| | | | |
|---|---|---|---|
| 6,641,565 B1 | 11/2003 | Lavi et al. | |
| 2011/0166543 A1* | 7/2011 | Stepovich | A61J 1/2096 604/413 |
| 2013/0046270 A1* | 2/2013 | Foshee | A61M 5/1782 604/407 |
| 2013/0110039 A1 | 5/2013 | Just | |
| 2014/0124514 A1 | 5/2014 | Onpharma | |
| 2015/0065993 A1 | 3/2015 | Arocha | |

\* cited by examiner

APPARATUS AND METHOD FOR NEUTRALIZING LOCAL ANESTHETIC

CROSS-REFERENCE TO RELATED APPLICATIONS

This application claims the benefit of U.S. Provisional Patent Application Ser. No. 62/608,144, filed Dec. 20, 2017, which is incorporated herein by reference in its entirety.

BACKGROUND

Local anesthetics are used in many medical and dental applications to reduce patient pain and discomfort. They are broadly used to anesthetize body tissues of all types. For example, one of the most common anesthetic procedures is the inferior alveolar nerve block (IANB) used in many dental procedures to anesthetize mandibular teeth, typically with anesthesia of the lower lip, chin, and parts of the tongue.

Although other local anesthetics may sometimes be used, lidocaine is the most commonly used local anesthetic in dental and medical procedures. After injection, a standard administration of lidocaine typically begins working within minutes and usually lasts for a few hours. Typically, it is mixed with a small amount of a vasoconstrictor, such as epinephrine, to reduce bleeding and delay resorption of the lidocaine. To have suitable shelf life and to increase suitability, lidocaine and other anesthetics are typically provided as a relatively acidic solution. For example, lidocaine is commonly provided as lidocaine hydrochloride 2% with a pH of about 3.5 to 3.9.

When injected, the acidity of the injected solution causes a painful stinging sensation until the solution becomes neutralized to physiological pH within the tissue at the injection site. Such pain is obviously undesirable, particularly in situations where the patient may already be anxious about needle injections and the upcoming procedure. For young children, in particular, the additional stinging sensation can be quite traumatic. Patient agitation can also make the injection procedure more difficult to administer, further exacerbating the problem.

Some practitioners will neutralize the local anesthetic by manually mixing an amount of a sodium bicarbonate solution with the lidocaine. In the medical and dental industries, this is sometimes referred to as "buffering", or "alkalization" of the anesthetic. For example, rather than directly loading an off-the-shelf lidocaine ampule or cartridge (often known as "carpule") into an aspirating syringe, the practitioner may use another syringe (e.g., a conventional insulin syringe) to manually remove some of the lidocaine from the carpule. With the additional space made available in the carpule, a suitable amount of sodium bicarbonate solution is then added to neutralize/buffer the anesthetic. Once neutralized, the anesthetic and/or vasoconstrictor lose efficacy relatively rapidly, and must be used within minutes of being neutralized.

The manual method of neutralization has several limitations. It requires the use of additional syringes to both remove some of the lidocaine from the carpule and to add the sodium bicarbonate solution, and it requires several manual steps that use up valuable practitioner time. In addition, whenever the use of sharps is increased, the risk of accidental needle sticking is likewise increased. Further, manual neutralization method is prone to user error, which may lead to miscalculated dosages, improper neutralization, and/or over-dosing of the anesthetic, for example. For reasons such as these, a typical dentist or other medical practitioner may simply forego the hassle of manually neutralizing the anesthetic.

Certain mixing devices for neutralizing local anesthetic are also available. For example, one device is a mixing pen with a buffer cartridge of sodium bicarbonate loaded at the rear section of the pen and a receptacle for holding the anesthetic carpule at the front section of the pen. A straight needle extends from the sodium bicarbonate cartridge and pierces the diaphragm of the carpule. A second straight needle also extends from the carpule diaphragm to expel excess anesthetic into a waste reservoir as the sodium bicarbonate is forced into the anesthetic carpule. Despite some advantage over manual mixing, the use of such mixing pens has several limitations. For example, such devices are designed to replace the standard armamentarium associated with local anesthetic delivery, meaning each dental room in a dental office would need its own mixing pen, and personnel would need significant retraining to properly use the new device. Also, they may require constant product replacement and daily maintenance as use of open sodium bicarbonate solution is limited to only a few days. Furthermore, many have an increased exposure to sharps. Dentists and other practitioners who have been trained using conventional armamentarium may be averse to upending long-term habits and office practices. In addition, such a device typically requires "priming" and other relatively complicated setup procedures before they can be readily used. Also, while there may be less exposure to sharps as compared to manual buffering, assembly of the pen and attachment of a new anesthetic carpule still exposes the user to more sharps than if no buffering were performed.

Other available systems are designed to function as a centralized station where multiple-dose containers of anesthetic and buffer are stored. The buffer and anesthetic are mixed and placed into a holding reservoir by actuating a button pump at the station. The dentist may then withdraw the buffered anesthetic from the holding reservoir. Such centralized system is impractical in a multi-room dental office where it may be prohibitively expensive to put a unit in each room and likewise undesirable for practitioners to move to and from a central loading location. Another limitation is the heightened risk of cross-contamination where different syringes are all making use of the same base station. Wasted components and solution may also be an issue. Where larger containers of sodium bicarbonate and anesthetic are used, there is greater risk that the materials will go bad prior to use. For example, opening/accessing a new container of sodium bicarbonate for only a few doses right before the weekend may lead to wasted product since the remaining solution will be unusable by the next working day. Such a system also requires custom syringe designs for docking with the station and cannot be used with conventional armamentarium, and as stated above, many practitioners may be averse to upending habits and practices that they are accustomed to.

Accordingly, there is a long felt and ongoing need for improved devices and methods for neutralizing a local anesthetic. Such devices and methods should be sufficiently simple to be easily incorporated into a typical dental or medical practice without excessive cost, without disrupting the use of conventional and time tested practices and equipment, and without introduction of human error.

SUMMARY

Disclosed herein are apparatus and methods for neutralizing a local anesthetic prior to injection into a patient.

Example devices are configured to provide rapid neutralization of the local anesthetic prior to its intended use in a patient (e.g., within seconds or minutes before use, such as within about 5 seconds to about 60 minutes). Administration of a neutralized local anesthetic reduces or eliminates the sharp stinging pain associated with administration of an acidic local anesthetic, and in addition increases the rate of onset anesthesia and increases the profundity of anesthesia.

In some embodiments a device for neutralizing a local anesthetic comprises:
an outer housing having a first end and a second end;
an inner housing at least partially disposed within the outer housing and being translatable within the outer housing, the inner housing having an anesthetic carpule receptacle and a buffer carpule receptacle; and
a transfer needle disposed at the first end of the outer housing, the transfer needle having a curved shape such that each of two ends point substantially toward the second end of the outer housing,
wherein the device is configured to move from a pre-deployed state in which the buffer carpule is not in contact with the transfer needle to a deployed state in which the inner housing is brought closer to the first end of the outer housing to bring the buffer carpule into contact with the transfer needle.

A buffer carpule containing a buffer solution can be preloaded within the buffer carpule receptacle, or it can be inserted into the receptacle by a user prior to or during use. Similarly, an anesthetic carpule containing an anesthetic solution can be preloaded with the anesthetic carpule receptacle, or it can be inserted into the receptacle by a use prior to or during use.

A method of neutralizing an acidic anesthesia solution comprises, providing an anesthesia neutralization device as disclosed herein, which may or may not be preloaded with one or both of a buffer carpule or anesthetic carpule. If not preloaded, one or both of the buffer carpule or anesthetic carpule can be loaded into the apparatus by the user. The user then actuates the anesthesia neutralization device to add the buffer solution to the anesthetic solution. Thereafter, the user can inject a patient at one or more injection sites with the buffered anesthetic solution.

Additional features and advantages will be set forth in part in the description that follows, and in part will be obvious from the description, or may be learned by practice of the embodiments disclosed herein. It is to be understood that both the foregoing brief summary and the following detailed description are exemplary and explanatory only and are not restrictive of the embodiments disclosed herein or as claimed.

BRIEF DESCRIPTION OF THE DRAWINGS

In order to describe the manner in which the above-recited and other advantages and features of the invention can be obtained, a more particular description of the invention briefly described above will be rendered by reference to specific embodiments thereof which are illustrated in the appended drawings. Understanding that these drawings depict only typical embodiments of the invention and are not therefore to be considered to be limiting of its scope, the invention will be described and explained with additional specificity and detail through the use of the accompanying drawings in which.

DETAILED DESCRIPTION

Introduction

The present disclosure relates to devices and methods for neutralizing a local anesthetic prior to injection into a patient. The devices described herein are configured to provide immediate neutralization of the local anesthetic just prior to its intended use in a patient (e.g., within seconds, minutes or hours before use, such as within about 5 seconds to about 24 hours, 12 hours, 6 hours, 3 hours, 2 hours, 60 minutes or 30 minutes). Administration of a neutralized local anesthetic reduces or eliminates the sharp stinging pain associated with administration of an acidic local anesthetic, and in addition increases the rate of onset anesthesia and increases the profundity of anesthesia.

Embodiments described herein include beneficial features that enable easy and effective neutralization of the local anesthetic, while virtually eliminating risks of accidental sticking with needles or improperly calculating the amount of neutralizing agent to use. Further, certain features provide for simple, single movement actuation of the device (e.g., one-handed operation) to carry out the neutralization. Certain features of the described embodiments allow dentists, doctors, or other medical practitioners to use the same equipment and other setup procedures with which they are accustomed. For example, following the neutralization, the neutralized carpule may be used in the dentist's preferred syringe just as any other standard carpule.

The term "carpule" as used herein is synonymous with "cartridge," "ampule," and other terms that may be used to describe the sealed container holding the anesthetic solution or the buffer/neutralization solution as the case may be. The term "carpule" is typically used in dental injection applications and so is the term most often used herein. However, use of term "carpule" is not intended to limit the described embodiments to dental applications.

Specific examples described herein are provided in the context of local anesthesia in dental applications. It will be understood, however, that the same concepts may also be utilized in other circumstances involving the administration of local anesthesia. For example, the devices and methods described herein may also be utilized to buffer anesthesia in a dermatological, plastic surgery, emergency room, paramedic, or general practice setting.

Further, in many examples the local anesthetic may specifically be referred to as lidocaine. However, it will be understood that the same principles described herein with respect to lidocaine may be used to neutralize other types of local anesthetics such as procaine, articaine (i.e., Septocaine®), bupivacaine (Marcaine®), mepivacaine (i.e., Carbocaine® and Polocaine®), novocaine, prilocaine (Citanest®), benzocaine, and combinations thereof, for example. Moreover, although the following description is focused particularly on neutralizing a local anesthetic just prior to use, it will be understood that the same components and principles may also be used in other applications in which the mixture of separate fluids is required or desired just prior to use.

Conventional Armamentarium for Local Anesthesia

Figure 1:
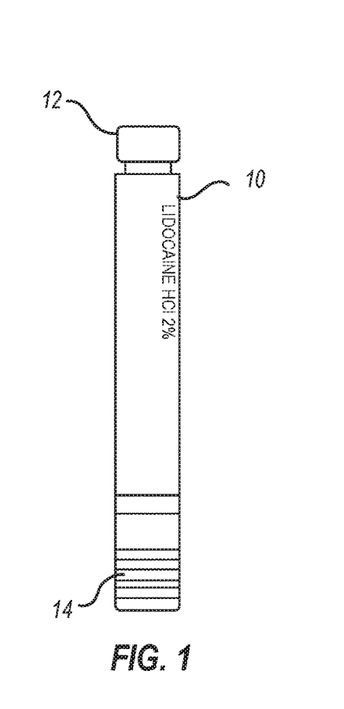
FIG. 1 illustrates a local anesthetic carpule commonly utilized in the dental field.
Figure 2A:
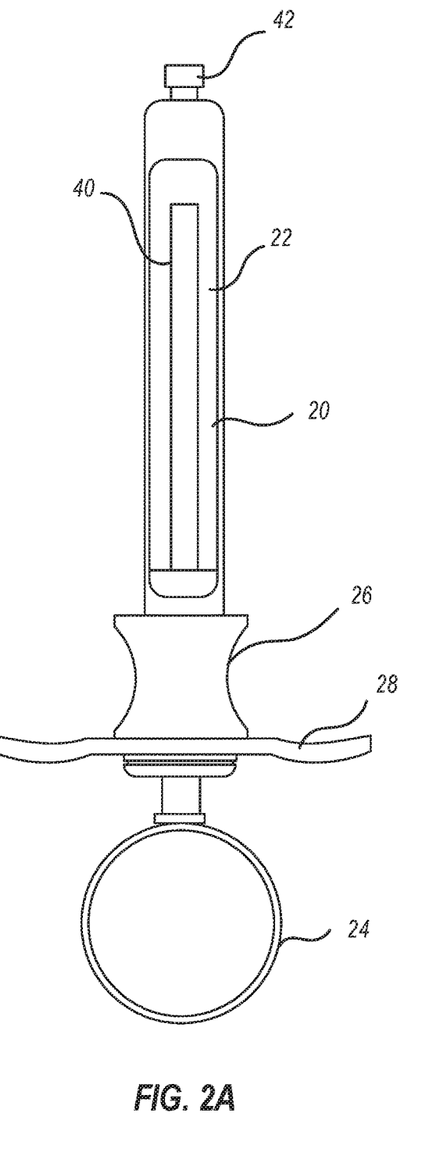
FIGS. 2A and 2B illustrate, respectively, an aspirating syringe and a disposable needle commonly utilized in the dental field.
Figure 2B:
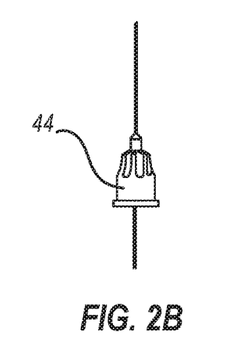

FIGS. 1 through 2B illustrate a standard anesthetic carpule 10 (lidocaine in this example), aspirating syringe 20, and disposable needle 44, respectively. The anesthetic carpule 10 is typically provided in a standard size with a length of about 2.5 inches (65 mm) and has a diaphragm 12 and a plunger 14 opposite the diaphragm 12. The aspirating syringe 20 is configured to receive the anesthetic carpule 10 into a correspondingly sized receptacle 22. As illustrated, an aspirating syringe 20 typically includes a thumb ring 24 or plunger, finger grip 26, finger bar 28, piston 40, and needle adaptor 42 to which the disposable needle 44 attaches. When used, an anesthetic carpule 10 is inserted into the receptacle 22 of the aspirating syringe 20, and a disposable needle 44 is attached to the needle adaptor 42. The user grips the syringe 20 with one hand by placing his/her fingers on the finger grip 26 and/or finger bar 28 and his/her thumb in the thumb ring 24. Moving the thumb ring 24 distally so as to be closer to the finger grip 26 causes the piston 40 to move distally, which presses the plunger 14 into the carpule and causes anesthetic to be expelled from the syringe 20.

Conventional devices such as those illustrated in FIGS. 1 and 2 are standard in a typical dental practice. Almost all dentists and other practitioners have been trained and continue to be trained using such devices and have gained valuable experience with their use. Most dental practices have operating procedures or habits that are established based on the use of such devices. The anesthesia neutralization devices described herein beneficially allow continued use of such devices with minimal or no disruption to known operating procedures, device preferences, and beneficial device experience. Maintaining continuity of mastered techniques benefits both the dental practitioner and the patient.

Anesthetic Neutralization Devices

Figure 3A:
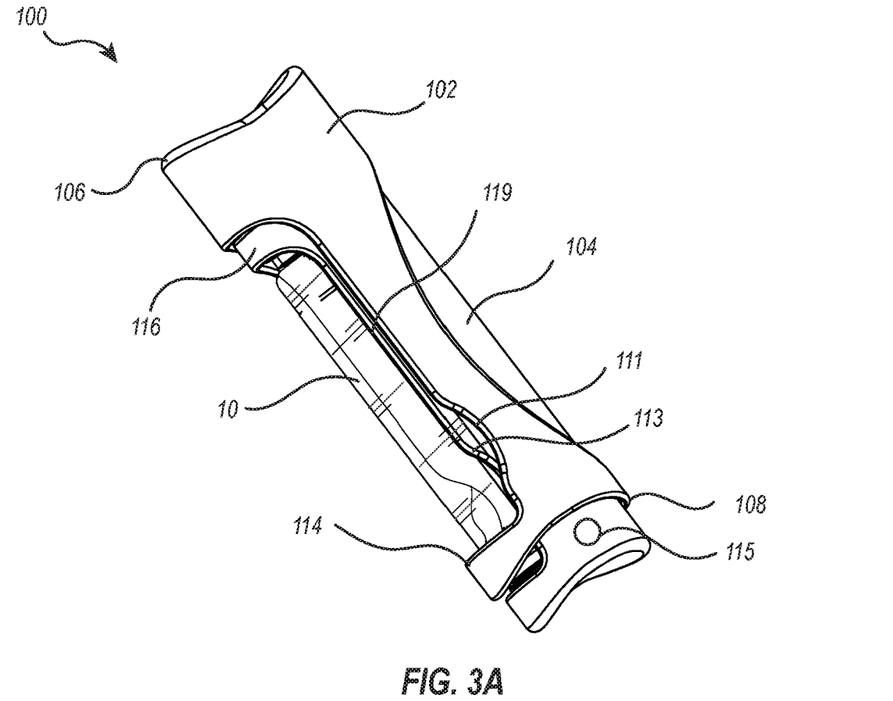
FIGS. 3A and 3B are isometric views of an exemplary anesthetic neutralization device in a pre-deployed and deployed state, respectively.
Figure 3B:
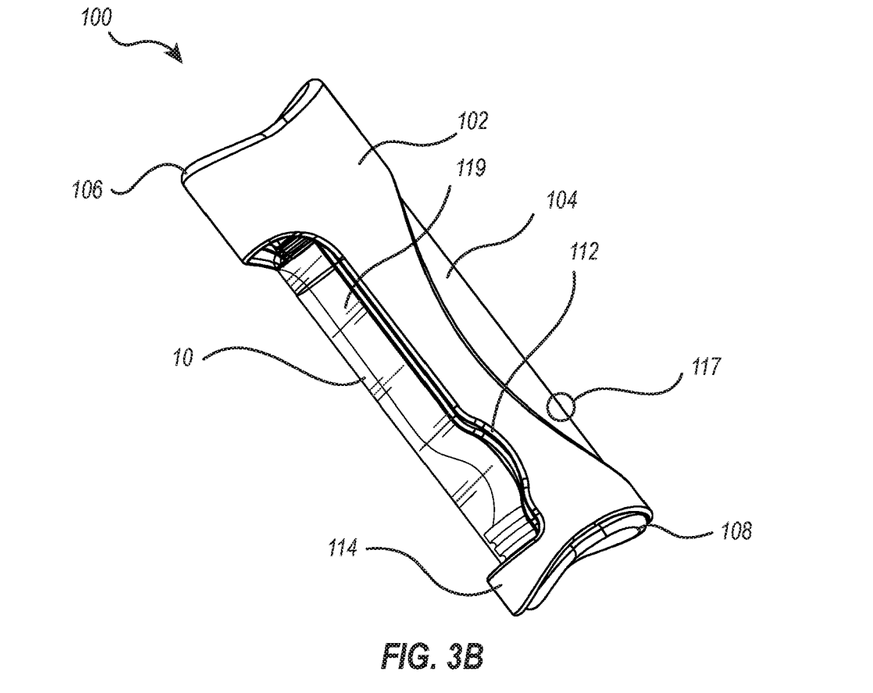

FIGS. 3A and 3B illustrate isometric views of an exemplary anesthesia neutralization device 100 with an anesthetic carpule 10 loaded therein. The anesthetic carpule 10 is visible through an elongate window formed through a side of the device 100 adjacent to the anesthetic carpule 10. FIG. 3A illustrates the device 100 in a pre-deployed state in which the anesthesia is still acidic, and FIG. 3B illustrates the device 100 after it has been actuated to at least partially neutralize the anesthetic. In some embodiments, the device 100 can be pre-loaded with the anesthetic carpule 10. Pre-loading prevents any confusion as to whether the carpule 10 has been neutralized or not. As explained in more detail below, the device 100 may include features which prevent removal of the carpule 10 until neutralization has occurred and may include features which prevent any "resetting" of the device to the pre-deployed state following actuation. This allows a user to determine whether the carpule 10 has been neutralized simply by determining whether it is currently removable from the device 100.

As further illustrated, the device 100 includes an outer housing 102 and an inner housing 104, which include the aforementioned window adjacent to the anesthetic carpule 10 through which the anesthetic carpule 10 can be seen. The outer housing 102 has a closed end 106 (also referred to herein as a first end 106) and an open end 108 (also referred to herein as a second end 108). The inner housing 104 fits within and is translatable within the outer housing 102. To actuate the device 100, a user may hold the device 100 between a thumb on one end and one or more fingers on the other end, for example. By compressing the two ends toward each other, the user moves the inner housing 104 and anesthetic carpule 10 further into the outer housing 102. The outer housing 102 and inner housing 104 are each partially open on the side of the device where the anesthetic carpule 10 is positioned. As explained in more detail below, the anesthetic carpule 10 may be removed through the opening after the device 100 has been actuated and the anesthetic has been neutralized.

On occasion, the first end 106 will be described as representing a "distal" direction, while the second end 108 will be described as representing a "proximal" direction, though these terms are arbitrarily assigned and are used herein only for convenience in describing relative positioning of certain device components. For example, if a first component is described as being located "distal" of or to a second component, the description is intended to indicate that the first component is disposed closer to the first end 106 than the second component.

Because of the open end 108 of the outer housing 102, the inner housing 104 can extend through the open end 108 and beyond the outer housing 102, as shown in FIG. 3A. When actuated, the inner housing 104 is brought further within the outer housing 102 and the inner and outer housings are substantially coextensive, as shown in FIG. 3B.

A portion of the outer housing 102 near the second end 108 defines a retention member 114 adjacent to the window and configured to hold the anesthetic carpule 10 in position within the device 100 until the device 100 has been actuated. A portion of the inner housing 104 is also configured as a lip 116, which extends around the diaphragm end of the carpule 10 and functions to retain the carpule 10 within the device on the end opposite the retention member 114.

The inner housing 104 further includes a flange 119 extending along its longitudinal axis where the inner housing contacts the carpule 10. The flange 119 (and another flange opposite flange 119) further provides retention of the carpule 10 by extending over the cylindrical curvature of the carpule 10. As shown in FIG. 3A, when the device 100 is in the pre-deployed state, the inner housing 104 extends somewhat beyond the open end of the outer housing 102, which brings the anesthetic carpule 10 into a position where the lip 116 and the retention member 114 function to prevent the anesthetic carpule 10 from being removed from the device 100 or from unintentionally falling out of the device 100 through the window.

Figure 9:
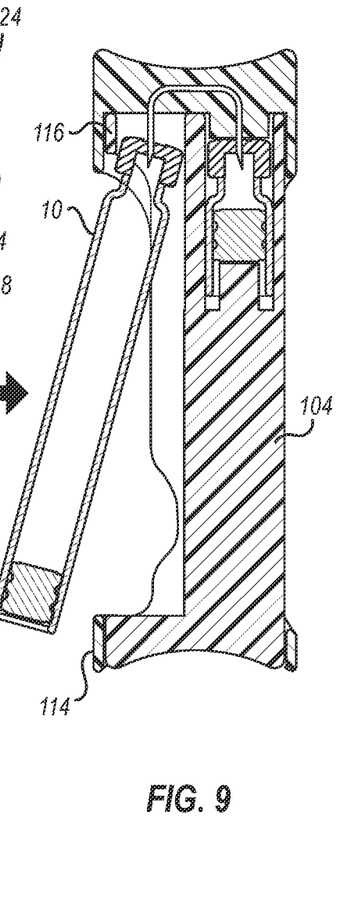

As shown in FIG. 3B, after the device 100 has been actuated by moving the inner housing 104 further into the outer housing 102, the anesthetic carpule 10 is moved enough toward the first end 106 to clear the retention member 114. From this position, the neutralized anesthetic carpule 10 may be removed through the window (as illustrated in FIG. 9) by pivoting the plunger end of the carpule 10 out and away from the device 100.

The illustrated device 100 also includes a gripping slot 112 formed when corresponding grooves 111 and 113 of the outer housing 102 and inner housing 104, respectively, align. The gripping slot 112 allows a user to grip the anesthetic carpule 10 and remove it from the device 100. As shown in FIG. 3A, when the device 100 is in the pre-deployed state, the grooves 111 and 113 are out of alignment. When the device 100 is actuated to the deployed state shown in FIG. 3B, the grooves 111 and 113 are brought into alignment to form the gripping slot 112. The gripping slot 112 beneficially provides space for the user to grip the anesthetic carpule 10 between two fingers to pivot the carpule 10 and remove it from the device 100.

The illustrated embodiment includes curved surfaces at each of ends 106 and 108. The curved surfaces may beneficially aid in gripping the device between a thumb and finger of the user during use. Although not shown, in some embodiments one or both of the ends 106 and 108 may include a grooved, dimpled, or otherwise textured surface to improve finger traction and grip when the device is being used. The illustrated embodiment may also include one or more indicators for providing an indication as to whether the anesthetic has been neutralized or not. For example, an indicator (e.g., word or symbol) may be placed at indicator location 115. Because indicator location 115 is visible when the device is in the pre-deployed state (FIG. 3A) but not in the deployed state (FIG. 3B), the indicator may read "Not Buffered," "Acidic," "Push To Actuate," "Squeeze To Actuate," or the like. Additionally, or alternatively, an indicator may be placed at indicator location 117. Because indicator location 117 is visible when the device is in the deployed state (FIG. 3B) but not in the pre-deployed state (FIG. 3A), the indicator may say "Buffered," "Neutralized," "Actuated," "Deployed" or the like.

Figure 4:
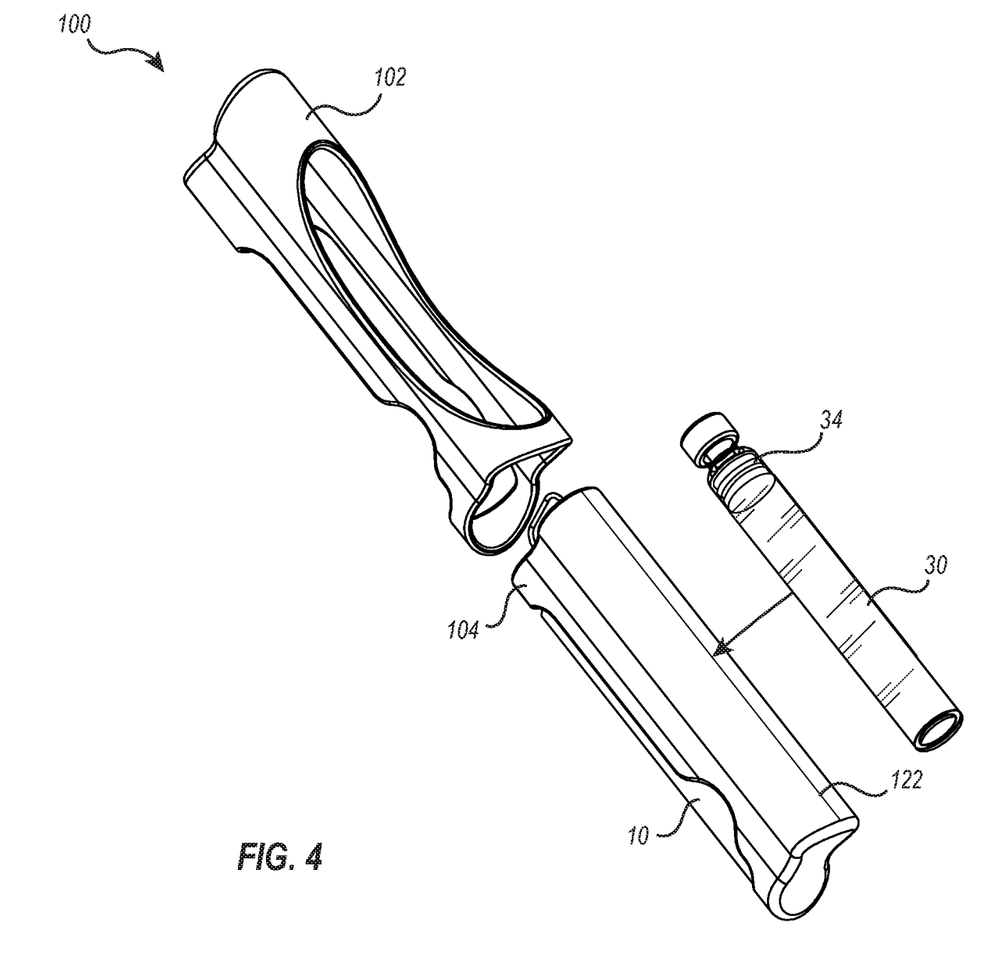
FIG. 4 is a view of the exemplary anesthetic neutralization device showing an optional structural slot allowing insertion of a buffer carpule during manufacture of the device.

FIG. 4 shows a partial exploded view of the device 100 showing an optional structural slot 122 that may be formed in the inner housing 104 to provide for insertion of the buffer carpule 30 during manufacture of the device. The structural slot 122 may be formed along the neutralization side of the inner housing 104 as shown. The inner housing 104 may be formed from a somewhat flexible polymer material that can flex enough to allow the slot 122 to open to allow insertion of the buffer carpule 30. Once the buffer carpule 30 is placed within the inner housing 104, the structural slot 122 biases toward the narrow, more closed position to retain the buffer carpule 30. Insertion of the inner housing 104 into the outer housing 102 also prevents the slot 122 from opening and thereby further retains the buffer carpule 30 in the proper position within the inner housing 104.

In the example shown in FIG. 4, the buffer carpule 30 is provided in the standard size of 65 mm (~2.5 inches). However, because the volume of neutralization solution required to neutralize the anesthetic is typically relatively small (e.g., 0.15 to 0.17 ml) compared to the volume of anesthetic, the plunger 34 may be located fairly close to the diaphragm end of the carpule 30. The excess length of the buffer carpule 30 may not be necessary but the inner housing 104 may still be configured to accommodate such length since carpules are typically available in standard sizes. Differently-sized anesthetic carpules 10 and/or buffer carpules 30 may also be utilized, such as the shorter version of the buffer carpule 30 shown in FIGS. 5 through 9, and the device need not be limited to standard sizes only.

Figure 5:
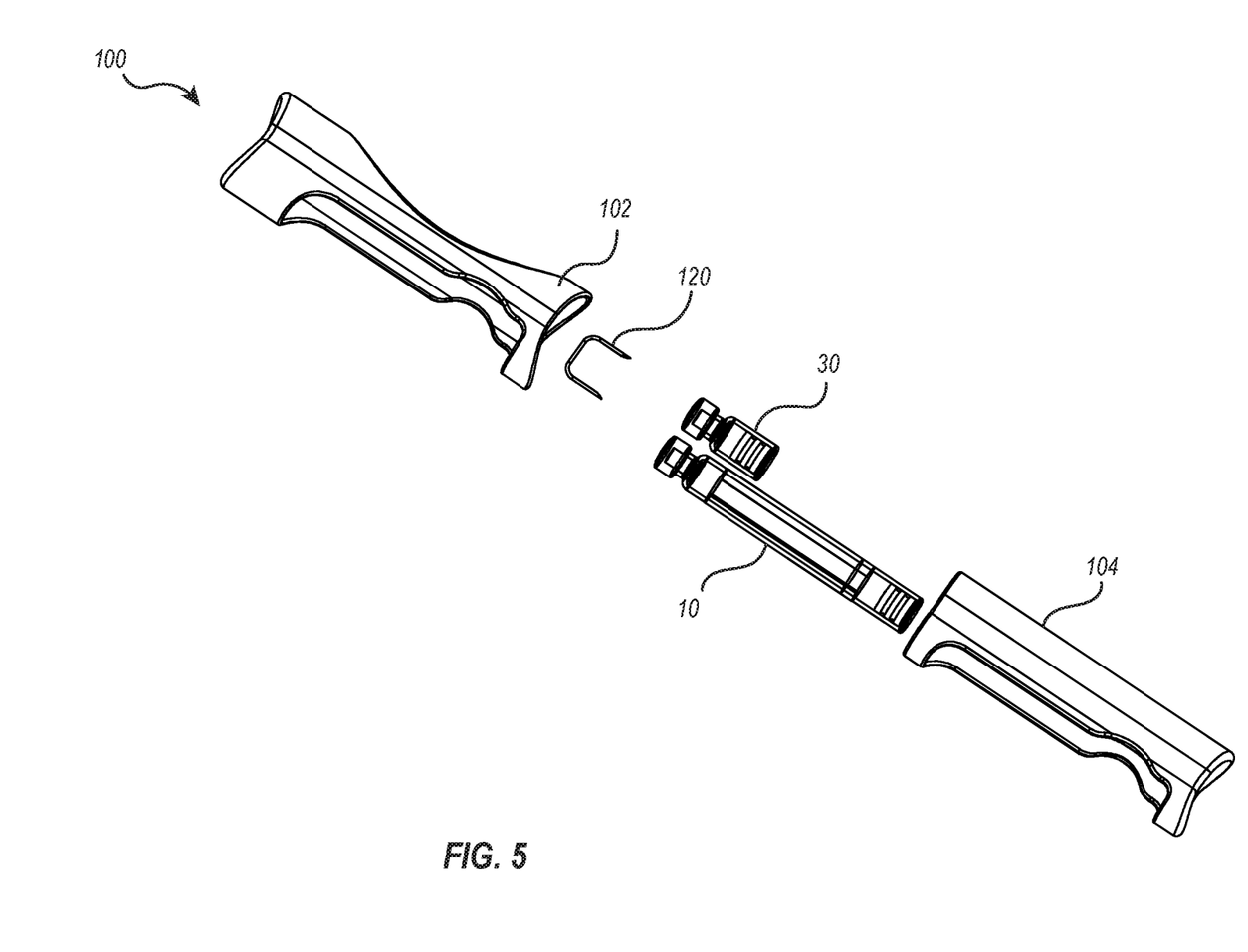
FIG. 5 is an exploded view of the exemplary anesthetic neutralization device.

FIG. 5 is an exploded view of the device 100 showing some of the inner components not visible in the views of FIGS. 3A, 3B, and 4. Adjacent the anesthetic carpule 10 is a buffer carpule 30. In this embodiment, the buffer carpule 30 is smaller than the anesthetic carpule 10. Other embodiments may include a buffer carpule of different size, such as a larger buffer carpule closer in size (or the same size) as the anesthetic carpule 10. The buffer carpule 30 includes a medically/dentally suitable neutralizing agent such as sodium bicarbonate, sodium hydroxide, other hydroxide, or combinations thereof.

Preferably, the buffer carpule 30 includes only about the amount of sodium bicarbonate (or other medically/dentally suitable neutralizing agent such as alkali metal carbonates or hydroxides such as sodium hydroxide) needed to neutralize the anesthetic. For example, a standard anesthetic carpule has 1.7 ml of anesthetic solution and requires about 0.17 ml of buffer solution. However, to ensure sufficient space within the anesthetic carpule 10 after addition of the buffer solution, it is preferred to use an anesthetic carpule 10 having about 1.55 ml of anesthetic solution and a buffer carpule 30 with about 0.15 ml of buffer solution. Of course, it will be understood that these particular volumes are exemplary only, and other embodiments may be configured to operate using carpules of different size or capacity in order to meet different application needs. For example, in a non-dental medical use, the amount of anesthetic utilized may be greater than the conventional 1.7 ml dental ampules, such as in the range of about 3 to 6 ml (including standard 3.4 ml and 5 ml units).

The foregoing anesthetic carpule 10 and buffer carpule 30 measurements assume a standard sodium bicarbonate concentration of 8.4% by weight as the buffer solution and a standard lidocaine HCl 2% solution as the anesthetic. One of skill in the art will understand that exact values may need to be adjusted to properly neutralize the anesthetic if a different anesthetic is used, the anesthetic has a different acidity (e.g., lidocaine HCl concentration may be within a range of about 0.5% to 4% or about 1% to 3%), a different buffer solution is used, a different buffer concentration is used (e.g., sodium bicarbonate concentration may be within a range of about 2% to 15%, or about 4% to 12%, or about 6% to 10%) and/or if different concentrations for either or both of the anesthetic or buffer are used, for example. In such cases, the volume of buffer required to neutralize the anesthetic may be readily determined using well understood chemical calculations.

As shown, the anesthetic carpule 10 and buffer carpule 30 are positioned side by side rather than end to end. A curved transfer needle 120 has openings on each end and is shaped so that one end enters the diaphragm of the anesthetic carpule 10 and one end enters the diaphragm of the buffer carpule 30. The transfer needle 120 is affixed within the outer housing 102 near the first end 106 such that when the inner housing 104 is pressed sufficiently far into the outer housing 102, the anesthetic carpule 10 and buffer carpule 30 are brought into contact with the opposing ends of the transfer needle 120. Beneficially, by being positioned within the outer housing 102, the sharp points of the transfer needle 120 need not be exposed, and the risk of users accidentally being stuck by the needle is essentially eliminated. In the illustrated embodiment, each end section of the transfer needle 120 has an equal length such that during actuation of the device 100, the anesthetic carpule 10 and buffer carpule 30 are punctured at substantially the same time. In alternative embodiments, the lengths may be differentiated such that the anesthetic carpule 10 and buffer carpule 30 are punctured at different times during actuation of the device and/or in the even the distal ends of the carpules are not longitudinally aligned.

Figure 6:
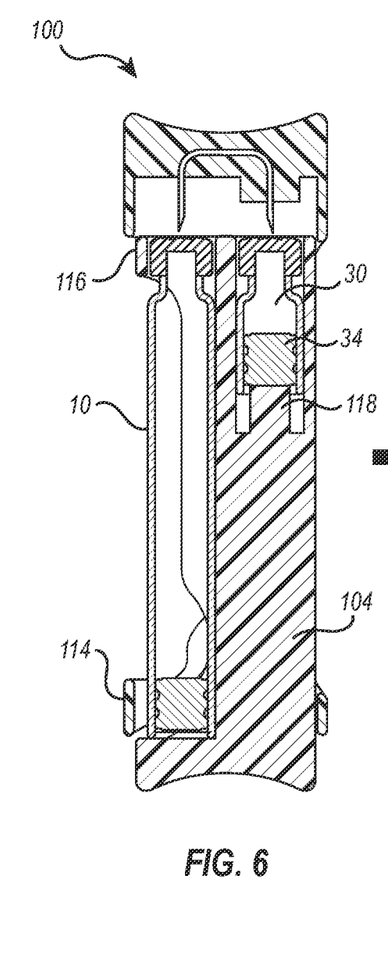
FIGS. 6 through 9 are cross-sectional views of the exemplary anesthetic neutralization device showing an operational sequence of moving the device from a pre-deployed state to a deployed state to prepare a carpule of neutralized anesthetic.

FIGS. 6 through 9 show the device in cross-section and illustrate actuation of the device 100 in sequence. FIG. 6 shows the device in a pre-deployed state (as in FIG. 3). As shown, the plunger end of the anesthetic carpule 10 is prevented from being removed from the device through the window by the retention member 114. The inner housing 104 also has a lip 116 that prevents the diaphragm end of the anesthetic carpule 10 from being removed through the window.

Figure 15:
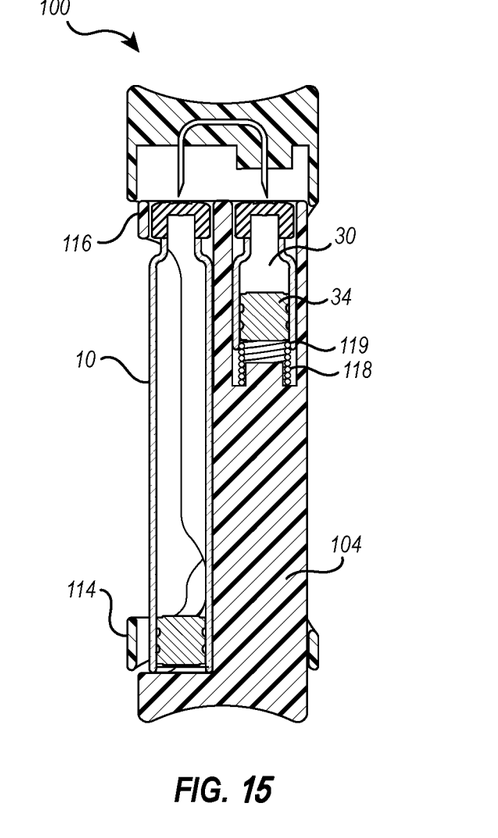
FIG. 15 illustrates an alternative embodiment of the device of FIG. 6 with a biasing spring.

The inner housing 104 includes a mandrel 118 configured to abut the plunger 34 of the buffer carpule 30 and to push the plunger 34 distally forward when the device 100 is actuated. Additionally, the mandrel 118 is configured to maintain adequate internal pressure of the solution within the buffer carpule 30 sufficient to prevent pressure-dependent changes to the chemical composition of the buffer solution. It has been found that if the buffer solution is not maintained under adequate pressure, it can degrade relatively rapidly. The device 100 may optionally include a biasing spring 119 (See FIG. 15) disposed proximal of the buffer carpule 30 between the buffer carpule and the inner surface of the inner housing 104. For example, when included, the spring 119 may be coiled around the mandrel 118. Alternatively, the mandrel 118 itself may be formed as a spring, such as spring 119, which once sufficiently compressed functions to push the plunger 34 distally forward. The spring 119 provides an outward force that biases the device 100 toward the pre-deployed position, which can beneficially prevent accidental actuation of the device until deliberate actuation occurs. When the device 100 is actuated, the outward biasing force of the spring 119 is overcome and the spring is collapsed into a compressed state. Other embodiments may omit the spring (as in FIGS. 6-9).

Figure 7:
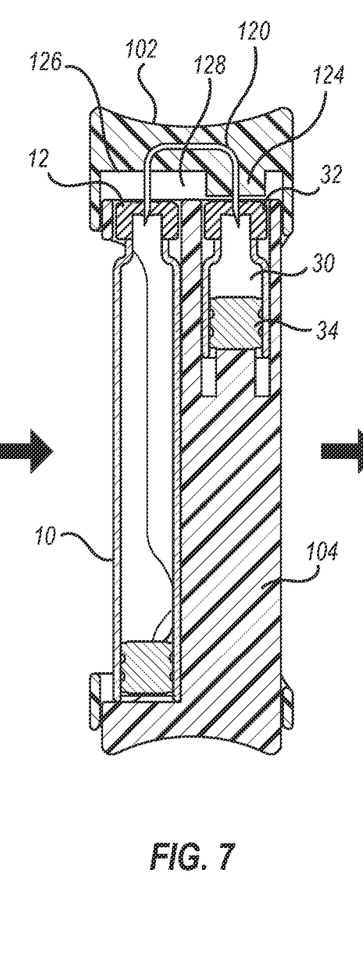

FIG. 7 shows the device 100 after partial actuation. As shown, the inner housing 104 has been moved enough to bring the diaphragms 12 and 32 into contact with respective ends of the transfer needle 120. However, the buffer solution has not yet been transferred from the buffer carpule 30 to the anesthetic carpule 10, as indicated by the position of the plunger 34. The outer housing 102 includes a buffer stop 124 configured to limit relative distal movement of the buffer carpule 30 and an anesthetic stop 126 configured to limit relative distal movement of the anesthetic carpule 10. At this mid-actuation point, the buffer carpule 30 has abutted against the buffer stop 124, whereas a space 128 still exists between the anesthetic carpule 10 and the anesthetic stop 126.

Figure 8:
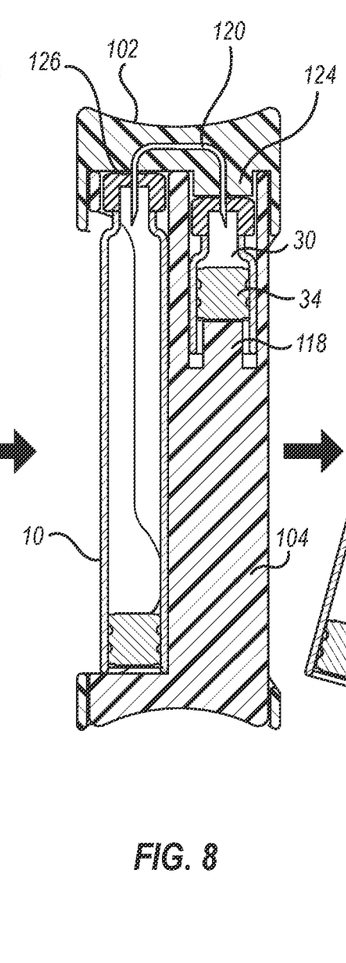

FIG. 8 shows the device 100 in the fully deployed state. Because of the height differential between the buffer stop 124 and the anesthetic stop 126, the anesthetic carpule 10 continues to move with the inner housing 104 as it is moved further distally into the outer housing 102. In contrast, the buffer carpule 30 is prevented from further distal movement and the inner housing 104 continues to move relative to the buffer carpule 30. This allows the mandrel 118 to push the plunger 34 distally forward, which causes the buffer solution to be expressed through the transfer needle 120 and into the anesthetic carpule 10. As shown, the amount of buffer solution transferred from the buffer carpule 30 to the anesthetic carpule 10 correlates to the length of buffer stop 124. The dosing of buffer solution may therefore be adjusted as desired by increasing or decreasing the length of buffer stop 124.

FIG. 9 shows removal of the anesthetic carpule 10 from the device 100 through the window after neutralization. As shown, although the lip 116 is still coincident with the diaphragm side of the anesthetic carpule 10, the plunger side of the carpule has cleared the retention member 114, allowing the plunger side of the carpule 10 to be pivoted away from the inner housing 104 and out of the device through the window. The neutralized anesthetic carpule 10 may then be utilized as needed using conventional armamentarium such as the conventional aspiration syringe shown in FIG. 2B or drawn into a conventional hypodermic needle, for example.

Figure 10:
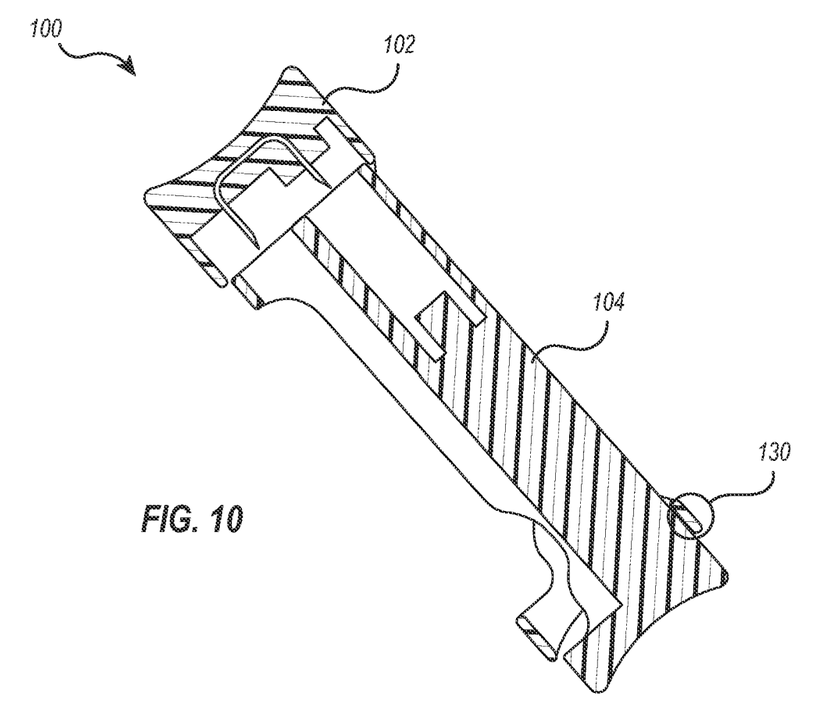
FIGS. 10 and 11 are cross-sectional views of the exemplary anesthetic neutralization device showing locations for one or more optional detents.
Figure 11:
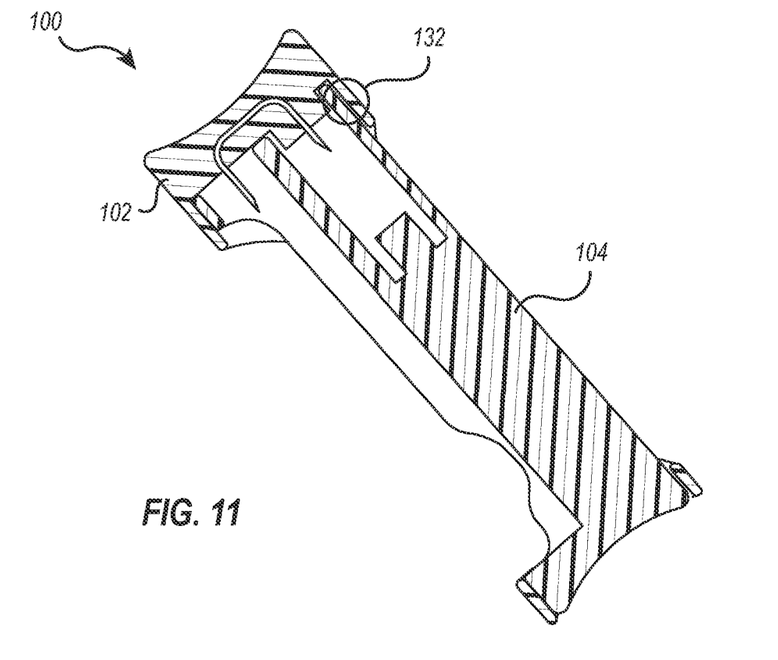

FIGS. 10 and 11 are cross-sectional views of the exemplary anesthetic neutralization device 100 showing locations for one or more optional detents. Some internal components have been removed for clarity. In preferred embodiments, the device 100 includes one or more detent features which limit movement of the outer housing 102 and inner housing 104 relative to one another. For example, the device 100 may include, at location 130, a proximal detent configured to prevent excessive proximal movement of the inner housing 104 relative to the outer housing 102 (e.g., to prevent the inner housing 104 from moving too far out of the outer housing 102), thereby keeping the anesthetic carpule within the device 100. The detent feature located at location 130 may wrap circumferentially around the device at that location.

The device may additionally or alternatively include, at location 132, a distal detent configured to prevent backwards (i.e., proximal) movement of the inner housing 104 after the device 100 has been actuated. The detent feature located at location 132 may wrap circumferentially around the device at that location. Preventing backwards movement of the inner housing 104 beneficially reduces the risk of confusion as to whether a given carpule has been neutralized or not. Under proper operation, the carpule is only removable after the device 100 has been actuated and the anesthetic has been neutralized. Preventing the device 100 from being "reset" to the pre-deployed state prevents any ambiguity as to whether neutralization has occurred. The detent locations indicated in FIGS. 10 and 11 are exemplary only, and other suitable detent locations may be additionally or alternatively used. The use of a detent may practically result in the device being only capable of a single use, which may be desirable, such as to prevent contamination.

Figure 12:
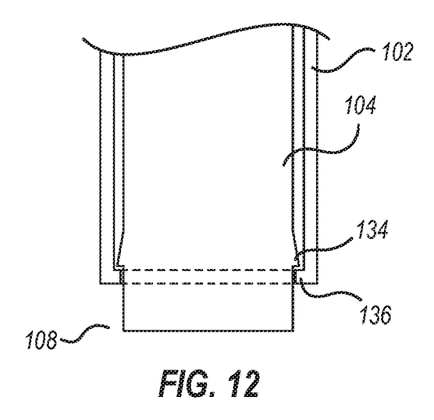
FIGS. 12 through 14 are detailed views of detent features which may be included in the anesthetic neutralization device.
Figure 13:
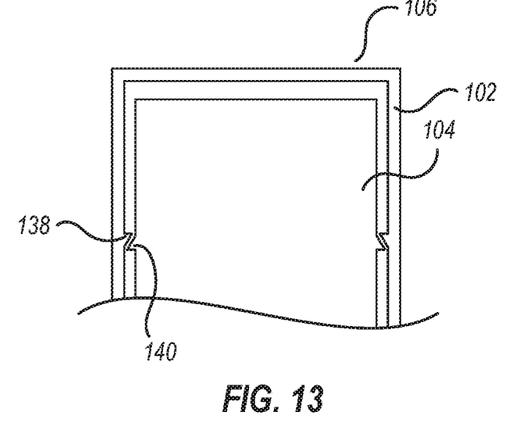
Figure 14:
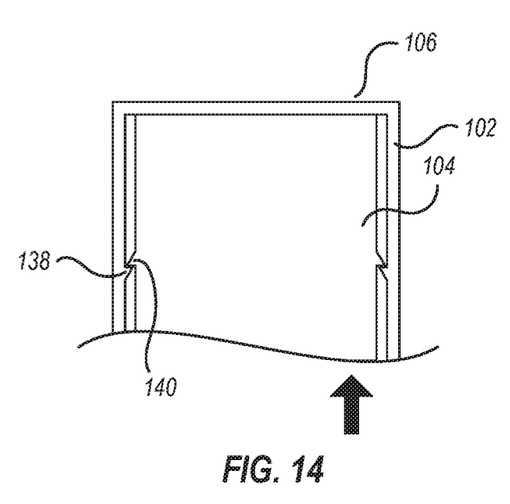

FIGS. 12 through 14 are detailed views of detent structures that may be utilized to limit relative movement between the outer housing 102 and inner housing 104. FIG. 12 shows a partial cross-sectional view of the second end 108 of the device. As shown, the inner housing 104 may include tab feature 134 and the outer housing may include corresponding tab feature 136. The corresponding tab features function to limit proximal movement of the inner housing 104 relative to the outer housing 102.

FIGS. 13 and 14 show partial cross-sectional views of the first end 106 of the device. FIG. 13 shows the device prior to full deployment and FIG. 14 shows the device in the fully deployed state. As shown in FIG. 13, corresponding tab features 138 and 140 have not yet engaged. Upon further distal movement of the inner housing 104, however, the tab feature 140 moves past the tab feature 138. The corresponding tab features 138 and 140 include angled surfaces that allow distal movement of the inner housing 104 until tab feature 140 moves past tab feature 138, but prevent proximal movement of the inner housing 140 after reaching the fully deployed position. Other embodiments may additionally or alternatively include other detent structures known in the art.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. A device for neutralizing a local anesthetic, comprising:
   an outer housing having a first end and a second end;
   an inner housing at least partially disposed within the outer housing and being translatable within the outer housing, the inner housing having an anesthetic carpule receptacle and a buffer carpule receptacle; and
   a transfer needle disposed at the first end of the outer housing, the transfer needle having a curved shape such that each of two ends point substantially toward the second end of the outer housing,
   wherein the outer housing includes an anesthesia stop and a buffer stop extending from the first end of the outer housing a distance toward the second end, the anesthesia stop and the buffer stop coinciding respectively with the anesthesia carpule receptacle and the buffer carpule receptacle of the inner housing,
   wherein the buffer stop extends further toward the second end than the anesthesia stop such that during actuation, a buffer carpule abuts against the buffer stop and upon further actuation, the inner housing continues to move relative to the buffer carpule to thereby force a buffer solution out of the buffer carpule and into the transfer needle,
   wherein the device is configured to move from a pre-deployed state in which the buffer carpule is not punctured by the transfer needle to a deployed state in which the inner housing is brought closer to the first end of the outer housing to cause the buffer carpule to be punctured by the transfer needle.

2. The device of claim 1, further comprising the buffer carpule disposed within the buffer carpule receptacle, the buffer carpule containing the buffer solution.

3. The device of claim 2, further comprising an anesthetic carpule disposed within the anesthetic carpule receptacle, the anesthetic carpule containing an anesthetic solution.

4. The device of claim 3, wherein the anesthetic solution includes lidocaine.

5. The device of claim 3, wherein the anesthetic carpule and the buffer carpule are oriented with respective diaphragms each facing toward the first end of the outer housing.

6. The device of claim 3, wherein the inner and outer housings define a window adjacent the anesthetic carpule receptacle to allow removal of the anesthetic carpule from the device.

7. The device of claim 6, wherein the outer housing includes a retaining member positioned to extend across a portion of the window when the device is in the pre-deployed state to thereby prevent the anesthetic carpule from being removed from the device, and which provides sufficient clearance for removal of the anesthetic carpule when the device is in the deployed state.

8. The device of claim 6, wherein the outer housing and inner housing each comprise corresponding grooves adjacent the window, the corresponding grooves being positioned such that when the device is in the deployed state, the grooves align to form a gripping slot in the window.

9. The device of claim 2, wherein the buffer solution includes sodium bicarbonate.

10. The device of claim 2, wherein the inner housing includes a mandrel disposed adjacent to the buffer carpule receptacle, the mandrel being sized to push a plunger of the buffer carpule forward when sufficiently forced against the plunger.

11. The device of claim 2, further comprising a biasing spring adjacent to the buffer carpule, the biasing spring being configured to provide an expansive force that biases the device toward the pre-deployed position.

12. The device of claim 11, wherein the expansive force provided by the biasing spring ensures that pressure within the buffer carpule is maintained when the device is in the pre-deployed state.

13. The device of claim 1, wherein the transfer needle has a U shape.

14. The device of claim 1, wherein the anesthetic carpule receptacle and the buffer carpule receptacle are arranged side by side.

15. The device of claim 1, wherein the outer housing is enclosed at the first end and open at the second end.

16. The device of claim 15, wherein the inner housing extends partially beyond the open second end of the outer housing.

17. The device of claim 1, wherein one or both of the first end of the outer housing and an opposing end of the inner housing opposite the first end have curved surfaces and/or textured surfaces for enhancing grippability.

18. A device for neutralizing a local anesthetic, comprising:
   an outer housing having an enclosed first end and an open second end;
   an inner housing at least partially disposed within the outer housing and being translatable within the outer housing, the inner housing having an anesthetic carpule receptacle, a buffer carpule receptacle, and a mandrel disposed adjacent to the buffer carpule receptacle, the mandrel being sized to push a plunger of a buffer carpule forward to move a buffer solution when the mandrel is sufficiently forced against the plunger;
   the buffer carpule disposed within the buffer carpule receptacle, the buffer carpule containing a buffer solution;
   an anesthetic carpule disposed within the anesthetic carpule receptacle, the anesthetic carpule containing an anesthetic solution; and
   a transfer needle disposed at the first end of the outer housing, the transfer needle having a curved shape such that each of two ends point substantially toward the second end of the outer housing,
   wherein the device is configured to move from a pre-deployed state in which the buffer carpule and anesthetic carpule are not punctured by the transfer needle to a deployed state in which the inner housing is brought closer to the first end of the outer housing to cause the buffer carpule and the anesthetic carpule to be punctured by the transfer needle,
   wherein the outer housing includes an anesthesia stop and a buffer stop extending from the first end of the outer housing a distance toward the second end, the anesthesia stop and the buffer stop coinciding respectively with the anesthesia carpule receptacle and the buffer carpule receptacle of the inner housing, and
   wherein the buffer stop extends further toward the second end than the anesthesia stop such that during actuation, the buffer carpule abuts against the buffer stop and upon further actuation, the inner housing continues to move relative to the buffer carpule to thereby force a buffer solution out of the buffer carpule and into the transfer needle.

19. A method of neutralizing an acidic anesthesia solution, comprising:
  providing a device for neutralizing a local anesthetic as in claim 18; and
  actuating the anesthesia neutralization device to add the buffer solution to the anesthetic solution.

20. A device for neutralizing a local anesthetic, comprising:
  an outer housing having a first end and a second end;
  an inner housing at least partially disposed within the outer housing and being translatable within the outer housing, the inner housing having an anesthetic carpule receptacle and a buffer carpule receptacle;
  a buffer carpule disposed within the buffer carpule receptacle, the buffer carpule containing a buffer solution;
  an anesthetic carpule disposed within the anesthetic carpule receptacle, the anesthetic carpule containing an anesthetic solution; and
  a transfer needle disposed at the first end of the outer housing, the transfer needle having a curved shape such that each of two ends point substantially toward the second end of the outer housing,
  wherein the inner and outer housings define a window adjacent the anesthetic carpule receptacle to allow removal of the anesthetic carpule from the device,
  wherein the device is configured to move from a pre-deployed state in which the buffer carpule is not punctured by the transfer needle to a deployed state in which the inner housing is brought closer to the first end of the outer housing to cause the buffer carpule to be punctured by the transfer needle.

21. The device of claim 20, wherein the outer housing includes a retaining member positioned to extend across a portion of the window when the device is in the pre-deployed state to thereby prevent the anesthetic carpule from being removed from the device, and which provides sufficient clearance for removal of the anesthetic carpule when the device is in the deployed state.

* * * * *

UNITED STATES PATENT AND TRADEMARK OFFICE
CERTIFICATE OF CORRECTION

PATENT NO. : 11,083,845 B2  
APPLICATION NO. : 16/225289  
DATED : August 10, 2021  
INVENTOR(S) : Johnson et al.

Page 1 of 1

It is certified that error appears in the above-identified patent and that said Letters Patent is hereby corrected as shown below:

In the Specification

<u>Column 8</u>  
Line 66, change "even" to –event–

Signed and Sealed this  
Fourth Day of January, 2022

Drew Hirshfeld  
*Performing the Functions and Duties of the*  
*Under Secretary of Commerce for Intellectual Property and*  
*Director of the United States Patent and Trademark Office*